US 7,645,268 B2

(12) United States Patent
Mickley et al.

(10) Patent No.: US 7,645,268 B2
(45) Date of Patent: Jan. 12, 2010

(54) NEEDLES AND METHODS OF USING SAME

(75) Inventors: Timothy J. Mickley, Elk River, MN (US); John E. Uschold, North Branch, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 241 days.

(21) Appl. No.: 10/808,357

(22) Filed: Mar. 25, 2004

(65) Prior Publication Data
US 2005/0215977 A1    Sep. 29, 2005

(51) Int. Cl.
*A61M 5/32* (2006.01)
*A61M 31/00* (2006.01)

(52) U.S. Cl. ...................... 604/274; 604/506
(58) Field of Classification Search ............ 604/506, 604/507, 511, 514, 522, 272–274, 170.03, 604/264, 187
See application file for complete search history.

(56) References Cited

U.S. PATENT DOCUMENTS

| 2,560,162 A * | 7/1951 | Ferguson ............... 604/274 |
| 2,717,599 A * | 9/1955 | Huber .................. 604/274 |
| 3,119,391 A | 1/1964 | Harrison |
| 3,788,320 A * | 1/1974 | Dye ................ 604/165.04 |
| 3,906,932 A * | 9/1975 | Ayres ................... 600/577 |
| 4,020,837 A * | 5/1977 | Larson ................. 604/411 |
| 4,368,738 A | 1/1983 | Tersteegen et al. |
| 4,537,593 A * | 8/1985 | Alchas ................. 604/411 |
| 4,753,641 A * | 6/1988 | Vaslow ................ 604/274 |
| 4,826,492 A * | 5/1989 | Magasi ................ 604/274 |
| 5,817,052 A * | 10/1998 | Johnson et al. .......... 604/506 |
| 5,843,048 A * | 12/1998 | Gross .................. 604/264 |
| 5,873,864 A * | 2/1999 | Luther et al. ............ 604/523 |
| 6,346,099 B1 * | 2/2002 | Altman ................ 604/528 |
| 2004/0191225 A1 * | 9/2004 | Dinsmore et al. ......... 424/93.7 |

FOREIGN PATENT DOCUMENTS

BE    631 225 A    8/1963
FR    2 057 353 A    5/1971

* cited by examiner

*Primary Examiner*—Matthew F Desanto
(74) *Attorney, Agent, or Firm*—Kenyon & Kenyon LLP

(57) ABSTRACT

A needle having a shaft with a distal end defining a distal opening. The shaft has a longitudinal axis that extends through the distal opening and the distal opening has a projected area that is smaller than a cross-sectional area of a section of the shaft proximal to the distal end of the shaft. Also provided are methods of directly delivering a therapeutic agent to a target site using a Huber needle or pencil-point needle.

23 Claims, 6 Drawing Sheets

NEEDLES AND METHODS OF USING SAME

FIELD OF THE INVENTION

The present invention relates to needles that minimize or prevent damage to the site in which the needles are inserted. The present invention also relates to methods of using needles for therapeutic purposes.

BACKGROUND

Needles have a wide variety of applications in the medical field. For instance, needles are used to delivery therapeutic agents, collect bodily fluids, and fill intravascular drug access devices. In many such applications, there is a desire to avoid or reduce damage to the site in which the needle is inserted. For example, intravascular drug access devices often include a chamber for holding a therapeutic agent and a pierceable rubber septum for receipt of a needle to either fill or empty the chamber. Repeated piercing of the septum with the needle can damage the septum leading to infusion of the septum fragments into the patient's vascular system or into any catheter or other device having access to the port, thereby occluding the port.

With respect to delivering a therapeutic agent to a target site in the body, particularly directly delivering a therapeutic agent to a target site, current injection needles have beveled open ends with Lancet point tips. Such open-ended needles have the potential to core tissue as the needles penetrate the tissue. In the case of directly delivering a therapeutic agent to a myocardial wall of the heart, since most myocardial direct injection procedures involve injecting a therapeutic agent into the left ventricle walls, the risk of tissue embolism into the left ventricular cavity exists.

Accordingly, there is a need for a needle that will prevent or minimize damage to the site in which the needle is inserted.

SUMMARY OF THE INVENTION

In one aspect, the present invention provides a needle comprising a shaft having a distal end defining a distal opening and having a longitudinal axis extending through the distal opening. The distal opening has a projected area that is smaller than a cross-sectional area of a section of the shaft proximal to the distal end of the shaft.

In another aspect, the present invention provides a method of directly delivering a therapeutic agent to a target site of a body other than the spinal cord by providing a drug delivery device comprising a Huber needle or pencil-point needle at the distal portion thereof and positioning the needle adjacent to the target site. The therapeutic agent is then directly delivered to the target site through the needle.

BRIEF DESCRIPTION OF THE DRAWINGS

The present invention will become more fully understood from the detailed description given hereinbelow and the accompanying drawings which are given by way of illustration only and wherein.

DETAILED DESCRIPTION OF THE INVENTION

Figure 1:
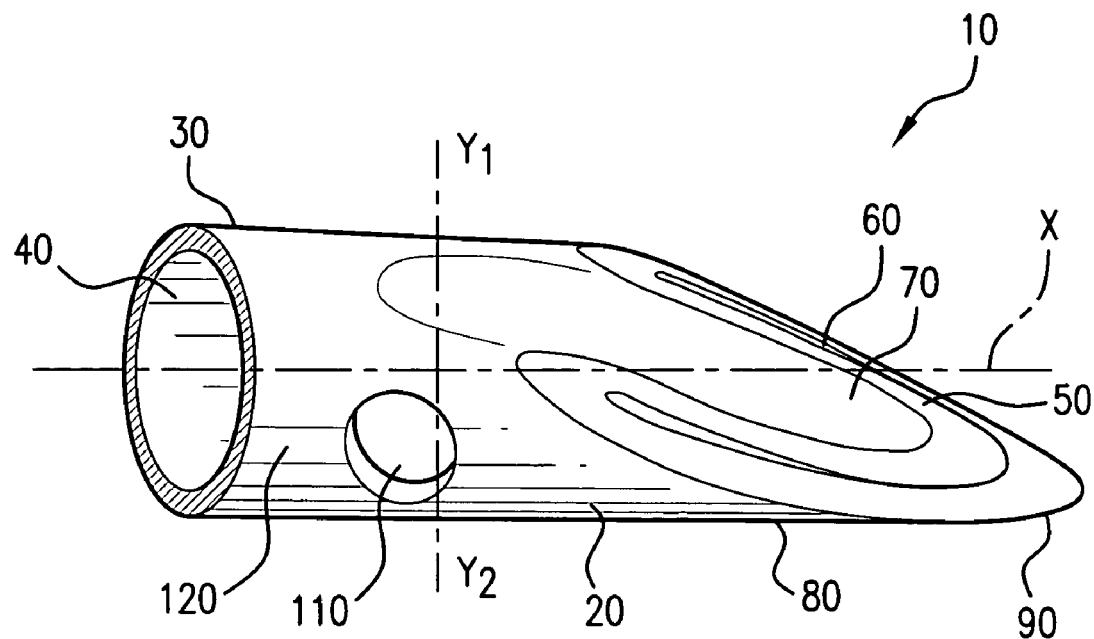
FIG. 1 is a side view of an embodiment of a needle according to the present invention.
Figure 2:
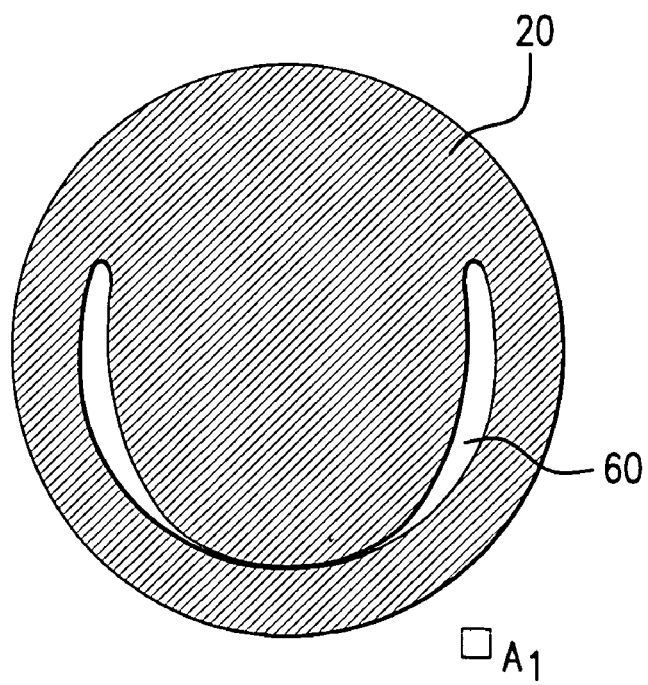
FIG. 2 illustrates the projection area of the distal opening of the embodiment of the needle depicted in FIG. 1.

Referring to FIG. 1, an embodiment of an aspect of the present invention provides a needle 10 comprising a shaft 20 having a proximal end 30 defining a proximal opening 40 and a distal end 50 defining a distal opening 60. A longitudinal axis X of shaft 20 extends through distal opening 60. The projected area A1 of distal opening 60, according to this aspect of the present invention, is smaller than a cross-sectional area of a section of shaft 20 proximal to distal end 50. As indicated in FIG. 2, projected area A1 of distal opening 60 is the area of distal opening 60 projected onto a plane perpendicular to longitudinal axis of shaft 20. To measure the cross-sectional area of a section of shaft 20, a cross-section of shaft 20 may be taken of any section of shaft 20 between proximal opening 40 and distal end 50. For example, as indicated in FIG. 1, a cross-section may be taken along lines $Y_1$ and $Y_2$.

Referring further to FIG. 1, in this embodiment, distal end 50 may comprise opposing first surface 70 and second surface 80 with first surface 70 being indented towards second surface 80. Distal end 50 may also terminate in a curvilinear tip 90, such as a rounded tip, as illustrated in FIG. 1. The degree of the curve of tip 90 is sufficiently blunt to avoid coring or excessive damage to the target site in which needle 10 is inserted but sufficiently pointed to pierce the target site.

Figure 3:
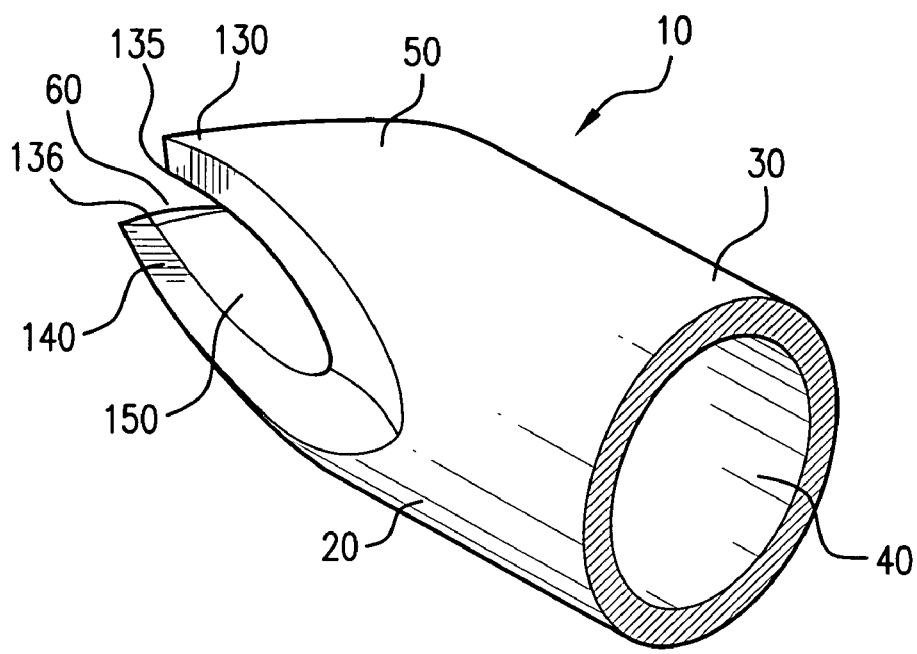
FIG. 3 is a perspective view of an alternative embodiment of a needle according to the present invention.
Figure 4:
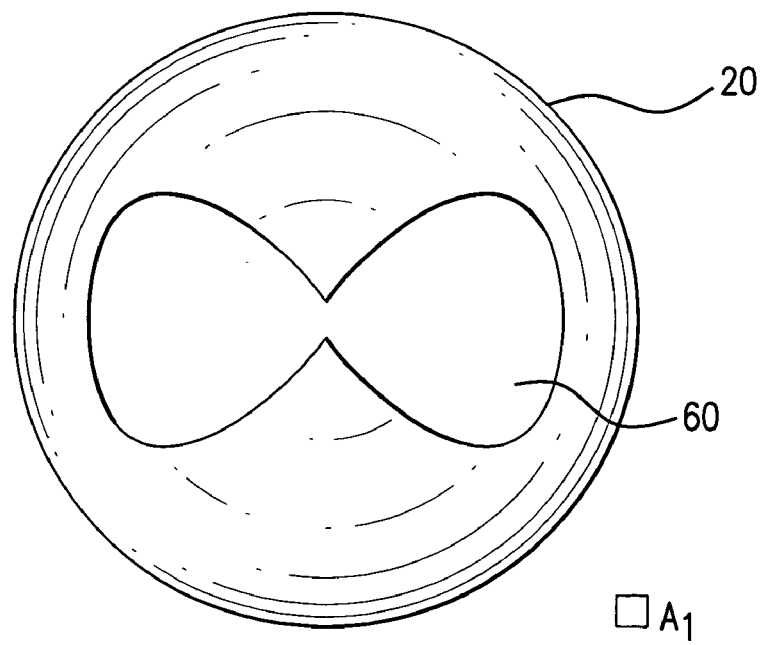
FIG. 4 illustrates the projection area of the distal opening of the embodiment of the needle depicted in FIG. 3.
Figure 5:
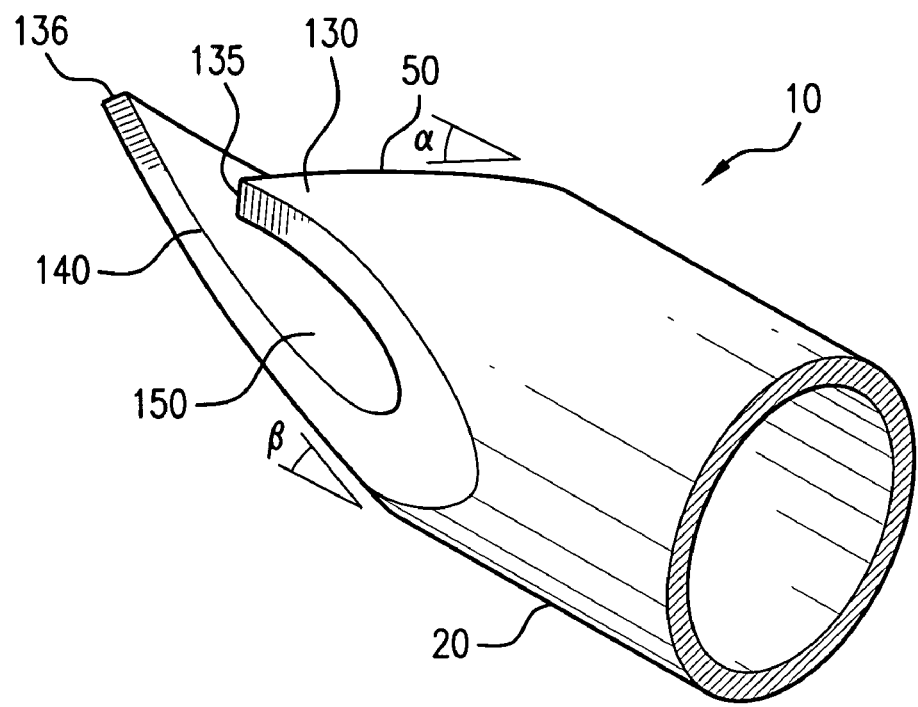
FIG. 5 is a perspective view of another embodiment of a needle according to the present invention.
Figure 6:
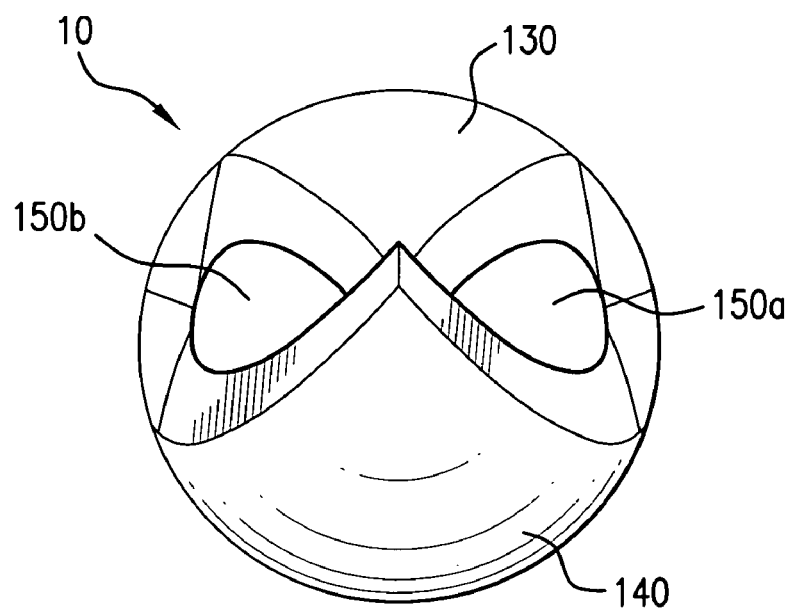
FIG. 6 is an end view of the embodiment of the needle illustrated in FIG. 5.
Figure 7:
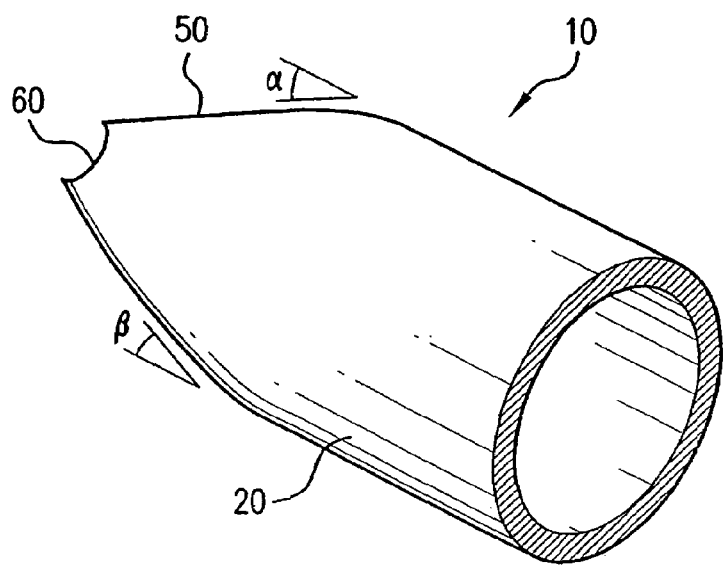
FIG. 7 is a perspective view of an alternative embodiment of a needle according to the present invention.

Referring to FIG. 3, in another embodiment of needle 10, distal end 50 comprises opposing first extension 130 and second extension 140 that are angled towards each other and whose tips 135 and 136 partially define distal opening 60. FIG. 4 depicts the projected area $A_1$ of distal opening 60, which is smaller than a cross-sectional area of a section of shaft 20 proximal to distal end 50 according to this aspect of the present invention. Referring to FIG. 5, in an alternative embodiment, second extension 140 is longer than first extension 130 in a direction parallel to longitudinal axis X of shaft 20. Preferably tips 135 and 136 of first and second extensions 130 and 140 are beveled, as illustrated in FIGS. 5 and 6. Further, as illustrated in FIGS. 5 and 6, first and second extensions 130 and 140 may mutually define at least one opening 150, which is offset from the longitudinal axis of shaft 20. Referring to FIG. 6, which is an end view of needle 10 illustrated in FIG. 5, preferably, first and second extensions 130 and 140 mutually define a pair of openings 150a and 150b that are each offset from longitudinal axis X. Although openings 150a and 150b are illustrated as being tear-drop shaped, such openings may have any shape. Referring to FIG. 7, in an alternative embodiment, distal end 50 does not include first and second extensions defining openings offset from axis X, but rather simply tapers towards distal opening 60. The degree in which distal end tapers can be any degree such that the projection area of distal opening 60 is smaller than a cross-sectional area of a section of shaft 20 proximal to distal end 50. For example, angle α and/or angle β, as indicated in FIGS. 5 and 7, may be from about 14° to about 30°.

In any of the embodiments of this aspect of the present invention, shaft 20 may comprise at least one port 110 on a side surface 120 thereof as depicted in FIG. 1. For example, shaft 20 may include a pair of ports 110 on opposing side surfaces of shaft 20. Whether shaft 20 has ports 110 may depend, for example, on the characteristics of the therapeutic agent that is delivered through shaft 20. For example, shaft 20 may comprise ports 110 if a high volume of a therapeutic agent and/or a therapeutic agent having a high viscosity is delivered through shaft 20 and shaft 20 may comprise no ports 110 if a low volume of a therapeutic agent and/or a therapeutic agent having a low viscosity is delivered through shaft 20. In embodiments where shaft 20 does comprise ports 110, such ports may be of any number, size, and shape.

Figure 8:
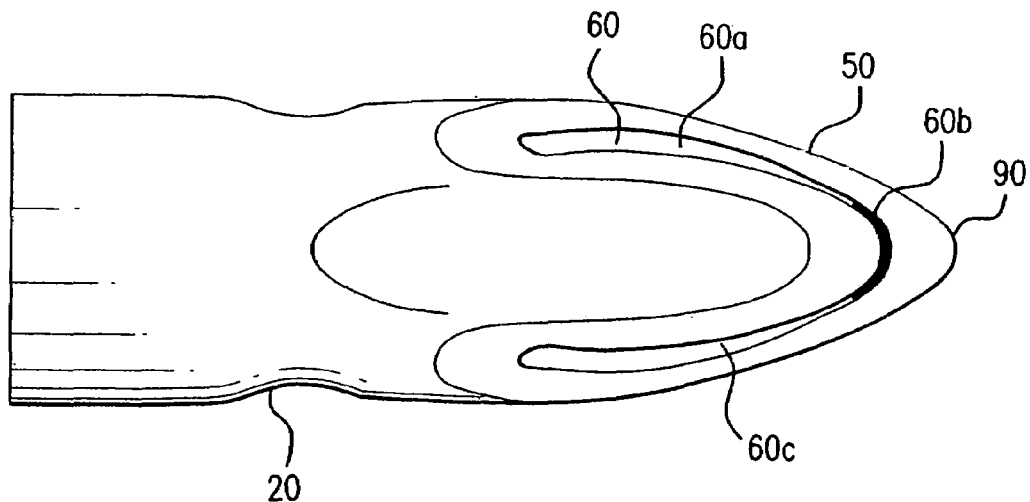
FIG. 8 is a top view of a needle according to the present invention depicting an alternative embodiment of the distal opening of the needle.

Furthermore, distal opening 60, according to this aspect of the present invention, may be a continuous opening or a discontinuous opening. For example, FIG. 8 illustrates a discontinuous distal opening 60 as section 60a of opening 60 is open, section 60b of opening 60 is closed near tip 90 and, section 60c is open. Of course, as will be understood by one in the art, distal opening 60 may have patterns of discontinuity other than the pattern illustrated in FIG. 8.

It should be emphasized that the above-described embodiments are merely exemplary and the present invention contemplates any design of needle 10 having a distal opening 60 through which longitudinal axis X extends and where distal opening 60 has a projected area A1 that is smaller than a cross-sectional area of a section of shaft 20 proximal to distal end 50.

The present invention also contemplates drug delivery devices, such as syringes or catheters, which have attached to the distal portions thereof, a needle according to any embodiment of this aspect of the present invention. Such drug delivery devices can be used to deliver any therapeutic agent to a target site of a body. To perform such delivery, a needle of this aspect of the present invention is attached to the distal portion of the drug delivery device and a therapeutic agent is loaded in the drug delivery device. The drug delivery device is placed in proximity to the target site and the needle is inserted in the target site. The therapeutic agent is then delivered through the needle to the target site of the body. Although a needle according to any embodiment of this aspect of the present invention has many applications and the needle is not in any way limited to a specific application, it is particularly useful for reducing or preventing coring or other damage to tissue. Accordingly, a needle according to any embodiment of this aspect of the present invention is particularly suited for direct delivery of a therapeutic agent to an organ or tissue, such as the myocardial wall of the heart, that is accessed from a blood vessel or from the blood stream and that when accessed by a needle, could result is a tissue core entering the blood stream.

A needle according to any embodiment of this aspect of the present invention can also be used to access a drug delivery port, such as an intravascular drug access device (IVAD). Such drug delivery ports are used for the delivery of therapeutic agents and are typically implanted in a subcutaneous pocket, such as the anterior upper chest wall below the clavicle. As mentioned previously, the drug delivery ports also usually include a chamber for the therapeutic agent and a pierceable septum for receipt of a needle to either fill or empty the chamber. According to the present invention, in order to access the drug delivery port, to delivery a therapeutic agent to the port for example, a drug delivery device, such as a syringe, is filled with a therapeutic agent and a needle according any embodiment of this aspect of the present invention is attached to the drug delivery device. The needle is inserted into the drug delivery port and the therapeutic agent is introduced into the drug delivery port through the needle. In instances where the drug delivery port includes a chamber covered with a septum, the needle pierces the septum to access the chamber to introduce the therapeutic agent to the chamber. Because of the particular configuration of the needle, damage to the septum is minimized even after repeated piercing of the septum. Of course, it will be understood to one of skill in the art that the needle can also be used to remove a therapeutic agent from the drug delivery port or to flush the drug delivery port with a saline solution, for example.

In another exemplary application, a needle according to any embodiment of this aspect of the present invention, is used to delivery a therapeutic agent to a spinal column of a body. For example, the needle can be used to delivery anesthesia, such as an epidural or spinal anesthesia, to the spinal column or to delivery any other drug intrathecally. Once again, because of the configuration of the needle, excessive damage to the affected area of the spinal column may be minimized or eliminated.

In addition to delivery of therapeutic agents to a target site of a body or an IVAD, a needle according to any embodiment of this aspect of the present invention, can be used to collect a fluid sample from a fluid containment site of a body. In such an application, the needle is attached to the distal portion of a drug delivery device and the needle is inserted into the fluid containment site of the body. A vacuum is created in the drug delivery device to collect the fluid sample from the fluid containment site. The fluid containment site can be any cavity, sac, or region in general of a body that stores or contains a fluid. Such fluids include, for example, blood, amniotic fluid, serous fluid, and cerebrospinal fluid. Accordingly, non-limiting examples of fluid containment sites include arteries and veins; the amniotic sac; serous cavities such as the peritoneal cavity, the pleural cavity, and the pericardial cavity; and the subarachnoid space.

It should be emphasized that the above mentioned methods of using a needle of any embodiment of this aspect of the present invention are merely illustrative and such needle can be used for any other appropriate purpose or application.

Figure 9:
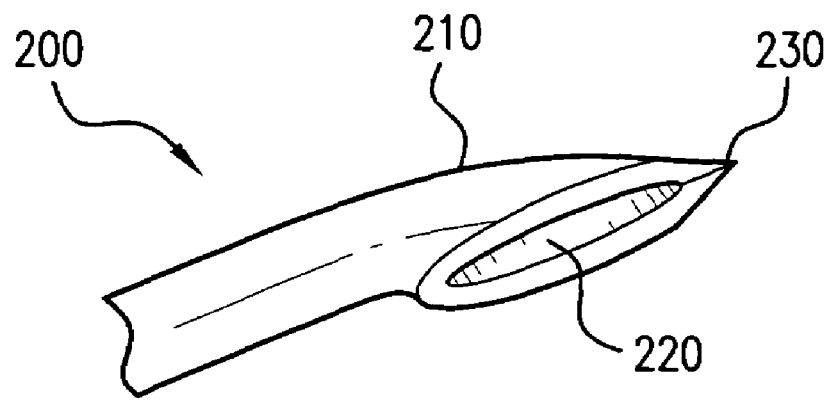
FIG. 9 is a perspective view of a Huber needle.
Figure 10:
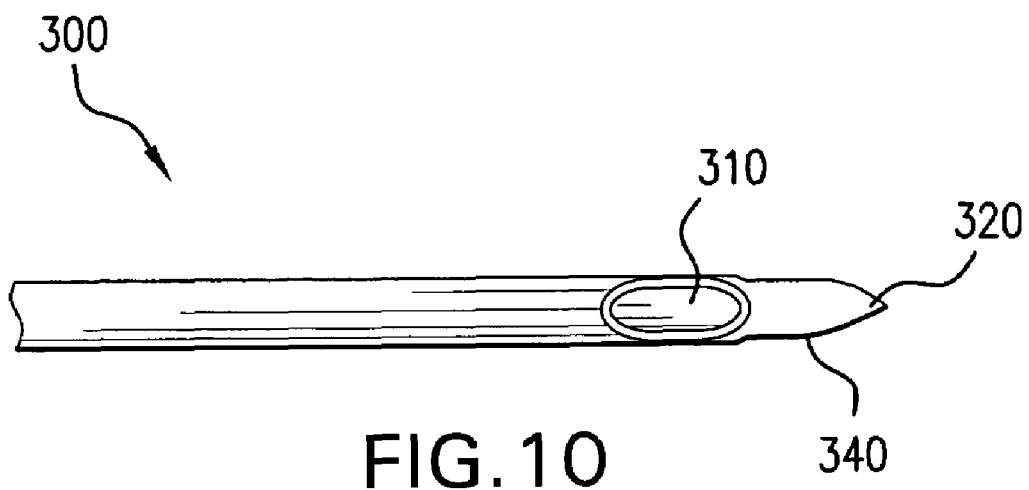
FIGS. 10-14 are side views of different types of "pencil-point" needles.
Figure 11:
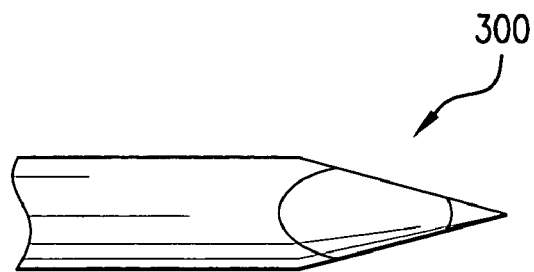
Figure 12:
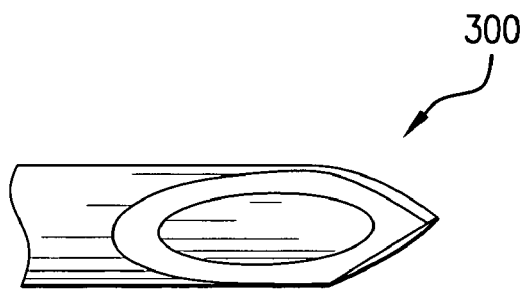
Figure 13:
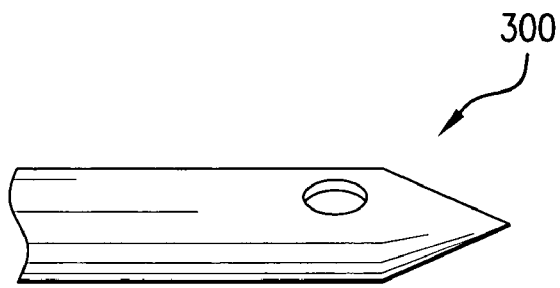
Figure 14:
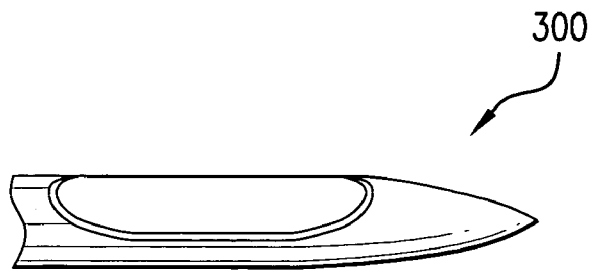

In another aspect, the present invention provides a method of directly delivering (as opposed to systemically delivering) a therapeutic agent to a target site of a body using a Huber needle, depicted in FIG. 9, or a "pencil point" needle, depicted in FIG. 10. In general, a Huber needle 200 has a distal portion 210 with a lateral bend and a laterally facing opening 220. The needle terminates in a sharpened tip 230. In general, a pencil-point needle 300 has a lateral opening 310 and a closed tip 320 at the distal end 340. According to this aspect of the present invention, a Huber needle 200 or a pencil point needle 300 is attached to the distal portion of a drug delivery device, such as a syringe or catheter. The needle 200 or 300 is then positioned adjacent to the target site and the therapeutic agent is delivered to the target site through needle 200 or 300.

Both the Huber needle and the pencil point needle are well-known in the art and further description of Huber needles are described, for example, in U.S. Pat. Nos. 2,409, 979, 2,717,599, and 2,748,769, all of which are incorporated herein by reference. The Huber needle to be used for direct delivery of a therapeutic agent includes safety Huber needles, straight Huber needles, and right-angled Huber needles. With respect to the pencil-point needle, this aspect of the present invention contemplates any type of pencil-point needle for direct delivery, including, for example, the designs illustrated in FIGS. 10-14.

The target site to which the therapeutic agent is delivered via the Huber needle or pencil-point needle according to this aspect of the present invention includes any target site other than the spinal cord. In a preferred embodiment, the target site is the heart and in an even more preferred embodiment, the target site is the myocardium.

In any of the aspects and embodiments of the present invention, the exact nature or identity of the therapeutic agent to be delivered will, of course, depend on the nature of the application of the needle and will be readily known to one in the art. For example, for direct delivery to the heart, the therapeutic agent may include anti-thrombogenic agents, anti-restenosis agents, angiogenic and anti-angiogenic agents, anti-inflammatory agents, anti-neoplastic/anti-proliferative/anti-mitotic agents, calcium entry blockers, anti-microbials, nitric oxide donors, anti-coagulants, vascular cell growth promotors, vascular cell growth inhibitors, vasodilating agents, agents which interfere with endogeneous vasoactive mechanisms, survival genes which protect against cell death, cells, and combinations thereof. Non-limiting examples of therapeutic agents for drug delivery into the spinal column, including intrathecal delivery, include anesthetics, analgesics, and chemotherapeutic agents.

In general, the therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, cladribine, 5-fluorouracil, methotrexate, doxorubicin, daunorubicin, cyclosporine, cisplatin, vinblastine, vincristine, epothilones, endostatin, trapidil, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homdimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugar, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

To provide controlled release of the therapeutic agents in embodiments where such a property is desired, the therapeutic agents may be microencapsulated with polymers to form a polymeric material/therapeutic agent matrix. When delivered into the target site, the therapeutic agent may released from the polymer as it slowly dissolves into the aqueous bodily fluids and diffuses out of the polymer.

As mentioned previously, certain aspects and embodiments of the present invention relate to delivering a therapeutic agent to a target site in a body. Unless described otherwise, non-limiting examples of such target sites include any body lumina and organ such as the coronary vasculature, esophagus, trachea, colon, biliary tract, urinary tract, prostrate, brain, lung, liver, heart, skeletal muscle, kidney, bladder, intestines, stomach, pancreas, ovary, cartilage, eye, bone, and the like.

Aspects and embodiments of the present invention can be used, for example, in any application for treating, preventing, or otherwise affecting the course of a disease or tissue or organ dysfunction. Such applications include inducing or inhibiting angiogenesis, preventing or treating restenosis, treating a cardiomyopathy or other dysfunction of the heart, treating Parkinson's disease, stroke or other dysfunction of the brain, treating cystic fibrosis or other dysfunction of the lung, treating or inhibiting malignant cell proliferation, treating any malignancy, and inducing nerve, blood vessel or tissue regeneration in a particular tissue or organ.

The foregoing description has been set forth merely to illustrate the invention and is not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

The invention claimed is:

1. A drug delivery device comprising:
    a catheter or syringe having a distal portion, and
    a needle attached to the distal portion, the needle comprising during use:
        a shaft having a distal end defining a distal opening and having a longitudinal axis extending through the distal opening,
        the distal opening having a projected area that is smaller than a cross-sectional area of the opening of the shaft proximal to the distal end of the shaft,
        the distal end comprising opposing first and second surfaces, wherein the first surface is indented towards the second surface to form a concavity on an outer portion of the first surface, and wherein the first surface blocks a majority of the distal opening.

2. The needle of claim 1, wherein the distal end of the shaft comprises at least one port on a side surface thereof.

3. The needle of claim 1, wherein the distal end of the shaft is tapered.

4. The needle of claim 1, wherein the distalmost end is a curvilinear blunt tip.

5. A method of delivering a therapeutic agent to a target site of a body comprising:
    providing a drug delivery device comprising:
        a non-coring needle having a distal end defining a distal opening and having a longitudinal axis extending through the distal opening,
        the distal end comprising a first surface indented towards a second surface to form a concavity on an outer portion of the first surface, wherein the first surface blocks a majority of the distal opening,
        the distal opening having a projected area that is smaller than a cross-sectional area of the opening of the shaft proximal to the distal end of the shaft,
    puncturing a body tissue with the non-coring needle tip; and
    delivering the therapeutic agent through the non-coring needle to a target site of a body.

6. The method of claim 5, wherein delivering the therapeutic agent comprises directly delivering the therapeutic agent to the target site.

7. The method of claim 6, wherein the target site is the heart.

8. The method of claim 6, wherein the target site is the myocardium.

9. The method of claim 5, wherein the target site is selected from a group consisting of the heart, lung, brain, liver, skeletal muscle, smooth muscle, kidney, bladder, intestines, stomach, pancreas, ovary, prostate and cartilage.

10. The method of claim 5, wherein the target site is a spinal column.

11. A method of accessing a drug delivery port comprising:
    providing a drug delivery device comprising:
        a non-coring needle having a distal end defining a distal opening and having a longitudinal axis extending through the distal opening,
        the distal end comprising a first surface indented towards a second surface to form a concavity on an outer portion of the first surface, wherein the first surface blocks a majority of the distal opening,
        the distal opening having a projected area that is smaller than a cross-sectional area of the opening of the shaft proximal to the distal end of the shaft; and
    inserting the needle of the drug delivery device into a drug delivery port to access the drug delivery port.

12. The method of claim 11, wherein accessing the drug delivery port comprises introducing a therapeutic agent through the needle into the drug delivery port.

13. The method of claim 11, wherein the drug delivery port comprises a septum, the needle of the drug delivery device piercing the septum to access the drug delivery port.

14. A method of collecting a fluid sample from a body comprising:
    providing a drug delivery device comprising:
        a non-coring needle having a distal end defining a distal opening and having a longitudinal axis extending through the distal opening,
        the distal end comprising a first surface indented towards a second surface to form a concavity on an outer portion of the first surface, wherein the first surface blocks a majority of the distal opening,
        the distal opening having a projected area that is smaller than a cross-sectional area of the opening of the shaft proximal to the distal end of the shaft;
    puncturing a body tissue with the non-coring needle;
    inserting the needle into a fluid containment site of a body; and
    creating a vacuum in the drug delivery device to collect a fluid sample from the fluid containment site of the body.

15. The method of claim 14, wherein the fluid sample comprises blood, amniotic fluid, serous fluid, or cerebrospinal fluid.

16. A drug delivery device comprising:
    a catheter or syringe having a distal portion, and
    a needle attached to the distal portion, the needle comprising during use:
        a shaft having a distal end comprising a first surface indented towards a second surface to form a concavity and to define a distal opening having a U-shape when viewed along the longitudinal axis from the front of the distal end,
        the shaft having a longitudinal axis extending through the distal opening, the distal opening having a projected area that is smaller than a cross-sectional area of a section of the shaft proximal to the distal end of the shaft.

17. The needle of claim 16, wherein the second surface is parallel to the longitudinal axis of the shaft.

18. The needle of claim 16, wherein the distalmost end is a curvilinear blunt tip.

19. The needle of claim 16, wherein the distal end of the shaft comprises at least one port on a side surface thereof.

20. A drug delivery device comprising:
   a catheter or syringe having a distal portion, and
   a needle attached to the distal portion, the needle comprising during use:
      a shaft having a distal end comprising a first surface indented towards a second surface to form a concavity and to define a distal opening, said distal opening being discontinuous and having a substantial U-shape when viewed along the longitudinal axis from the front of the distal end, wherein a bottom of the U-shape is closed,
      the shaft having a longitudinal axis extending through the distal opening,
      the distal opening having a projected area that is smaller than a cross-sectional area of a section of the shaft proximal to the distal end of the shaft.

21. The needle of claim 20, wherein the distalmost end is a curvilinear blunt tip.

22. The needle of claim 20, wherein the distal end of the shaft comprises at least one port on a side surface thereof.

23. The needle of claim 20, wherein the center of the concavity of the first surface is in contact with the second surface.

* * * * *

UNITED STATES PATENT AND TRADEMARK OFFICE
CERTIFICATE OF CORRECTION

PATENT NO. : 7,645,268 B2 Page 1 of 1
APPLICATION NO. : 10/808357
DATED : January 12, 2010
INVENTOR(S) : Mickley et al.

It is certified that error appears in the above-identified patent and that said Letters Patent is hereby corrected as shown below:

Column 3, line 65, "delivery" should be changed to --deliver--;
Column 4, line 1, "according any" should be changed to --according to any--;
Column 4, line 17, "delivery" should be changed to --deliver--;
Column 4, line 18, "delivery" should be changed to --deliver--;
Column 4, line 20, "delivery" should be changed to --deliver--;
Column 5, line 20, "promotors" should be changed to --promoters--;
Column 5, lines 21-22, "endogeneous vascoactive" should be changed to --endogenous vasoactive--;
Column 5, line 31, "such heparin" should be changed to --such as heparin--;
Column 5, line 40, "estrodiol" should be changed to --estradiol--;
Column 5, line 56, "lisidomine" should be changed to --linsidomine--;
Column 5, line 62, "Warafin" should be changed to --Warfarin--;
Column 5, line 64, "promotors" should be changed to --promoters--;
Column 6, lines 6-7, "endogeneus vascoactive" should be changed to --endogenous vasoactive--;
Column 6, line 20, "("MCP-1)" should be changed to --("MCP-1")--;
Column 6, line 21, "BMP's" should be changed to --BMPs--;
Column 6, line 24, "BMPS" should be changed to --BMPs--;
Column 6, line 26, "homdimers" should be changed to --homodimers--;
Column 6, line 30, "hedghog" should be changed to --hedgehog--;
Column 6, line 30, "DNA's" should be changed to --DNAs--;
Column 6, line 46, "sugar" should be changed to --sugars--;
Column 6, line 59, "may released" should be changed to --may be released--; and
Column 6, line 67, "prostrate" should be changed to --prostate--.

Signed and Sealed this

Twenty-second Day of June, 2010

David J. Kappos
*Director of the United States Patent and Trademark Office*